(12) United States Patent
Nakamura et al.

(10) Patent No.: US 7,641,610 B2
(45) Date of Patent: Jan. 5, 2010

(54) ENDOSCOPE ELECTRIC CONNECTION DEVICE

(75) Inventors: Naohiro Nakamura, Hachioji (JP); Masaaki Miyagi, Hachioji (JP); Seisuke Takase, Hachioji (JP); Hidenobu Kimura, Hachioji (JP)

(73) Assignee: Olympus Medical Systems Corporation, Tokyo (JP)

( * ) Notice: Subject to any disclaimer, the term of this patent is extended or adjusted under 35 U.S.C. 154(b) by 791 days.

(21) Appl. No.: 11/200,401

(22) Filed: Aug. 9, 2005

(65) Prior Publication Data

US 2007/0038024 A1  Feb. 15, 2007

(51) Int. Cl.
*A61B 1/04* (2006.01)
*A61B 1/00* (2006.01)

(52) U.S. Cl. .......................... 600/132; 600/110; 439/77
(58) Field of Classification Search .............. 600/101, 600/110, 112, 132; 439/55, 65, 67, 77, 95, 439/96, 494, 497, 626, 660; 361/749
See application file for complete search history.

(56) References Cited

U.S. PATENT DOCUMENTS

| | | | |
|---|---|---|---|
| 3,633,189 A | | 1/1972 | Billawala |
| 4,811,107 A | | 3/1989 | Bridges et al. |
| 4,957,109 A | * | 9/1990 | Groeger et al. ............. 600/391 |
| 4,974,075 A | * | 11/1990 | Nakajima ................... 348/75 |
| 5,844,783 A | * | 12/1998 | Kojima ...................... 361/777 |
| 6,348,035 B1 | * | 2/2002 | Takami ...................... 600/132 |
| 7,488,288 B2 | * | 2/2009 | Tanaka et al. .............. 600/459 |

FOREIGN PATENT DOCUMENTS

| | | | |
|---|---|---|---|
| EP | 1 549 117 A1 | | 6/2005 |
| EP | 1 839 559 A1 | | 10/2007 |
| JP | 02-129872 | | 5/1990 |
| JP | 06273653 A | * | 9/1994 |
| JP | 07327923 A | * | 12/1995 |
| JP | 2000354584 A | * | 12/2000 |
| WO | WO 2006/075744 A1 | | 7/2006 |

* cited by examiner

*Primary Examiner*—John P Leubecker
*Assistant Examiner*—Samuel Candler
(74) *Attorney, Agent, or Firm*—Scully, Scott, Murphy & Presser, P.C.

(57) ABSTRACT

An endoscope electric connection device accommodated within a scope connector for connecting an electronic endoscope and an external apparatus, the device including a first band having a first contact portion to which a signal line of a transmission cable for transmitting an image signal from an image pickup unit of the electronic endoscope is connected and a second contact portion to which a ground line of the transmission cable is connected, a second band having a third contact portion connecting to a connector for electrically connecting to the external apparatus and having flexibility, and a transmitting portion provided in the first band and second band for electrically connecting the first contact portion and second contact portion to the third contact portion, wherein the transmitting portion can keep electric connection between the first contact portion and second contact portion and the third contact portion even with the second band bent.

15 Claims, 15 Drawing Sheets

ENDOSCOPE ELECTRIC CONNECTION DEVICE

BACKGROUND OF THE INVENTION

1. Field of the Invention

The present invention relates to an endoscope electric connection device for use in an electric connector which connects to an external apparatus used in combination with an endoscope.

2. Description of the Related Art

An electric connector connecting to multiple cable lines is generally used for electrically connecting various electronic apparatuses.

An electronic endoscope apparatus, which is one of the electronic apparatuses, has an electronic endoscope internally containing an image pickup unit including a solid image pickup device to be inserted into a body cavity for shooting the inside of the body cavity. The electronic endoscope apparatus further includes a video processor, which is an external apparatus and performs predetermined signal processing on a shot signal shot by the electronic endoscope and generates an endoscope video signal.

The video processor and the electronic endoscope have multiple signal cable lines, which are electrically connected via an electric connector of the electronic endoscope for transmission/reception of various signals from the image pickup unit and supply of driving power to the image pickup unit.

A structure of the electric connector is disclosed in Japanese Unexamined Patent Application Publication No. 2-129872, for example. In the electric connector of the electronic endoscope, one end of each of multiple signal cable lines is connected to an image pickup unit having a solid image pickup device while the other end is connected to a corresponding connector pin separately and directly by soldering, for example.

SUMMARY OF THE INVENTION

An endoscope electric connection device accommodated within a scope connector for connecting an electronic endoscope and an external apparatus, the device including a first band part having a first contact portion to which a signal line of a transmission cable for transmitting an image signal from an image pickup unit of the electronic endoscope is connected and a second contact portion to which a ground line of the transmission cable is connected, a second band part having a third contact portion connecting to a connector for electrically connecting to the external apparatus and having flexibility, and a transmitting portion provided in the first band part and second band part for electrically connecting the first contact portion and second contact portion to the third contact portion, wherein the transmitting portion can keep electric connection between the first contact portion and second contact portion and the third contact portion even with the second band part bent.

The above and other objects, features and advantages of the invention will become more clearly understood from the following description referring to the accompanying drawings.

DETAILED DESCRIPTION OF THE PREFERRED EMBODIMENTS

An electronic endoscope system according to present embodiments will be described below with reference to drawings.

Figure 1:
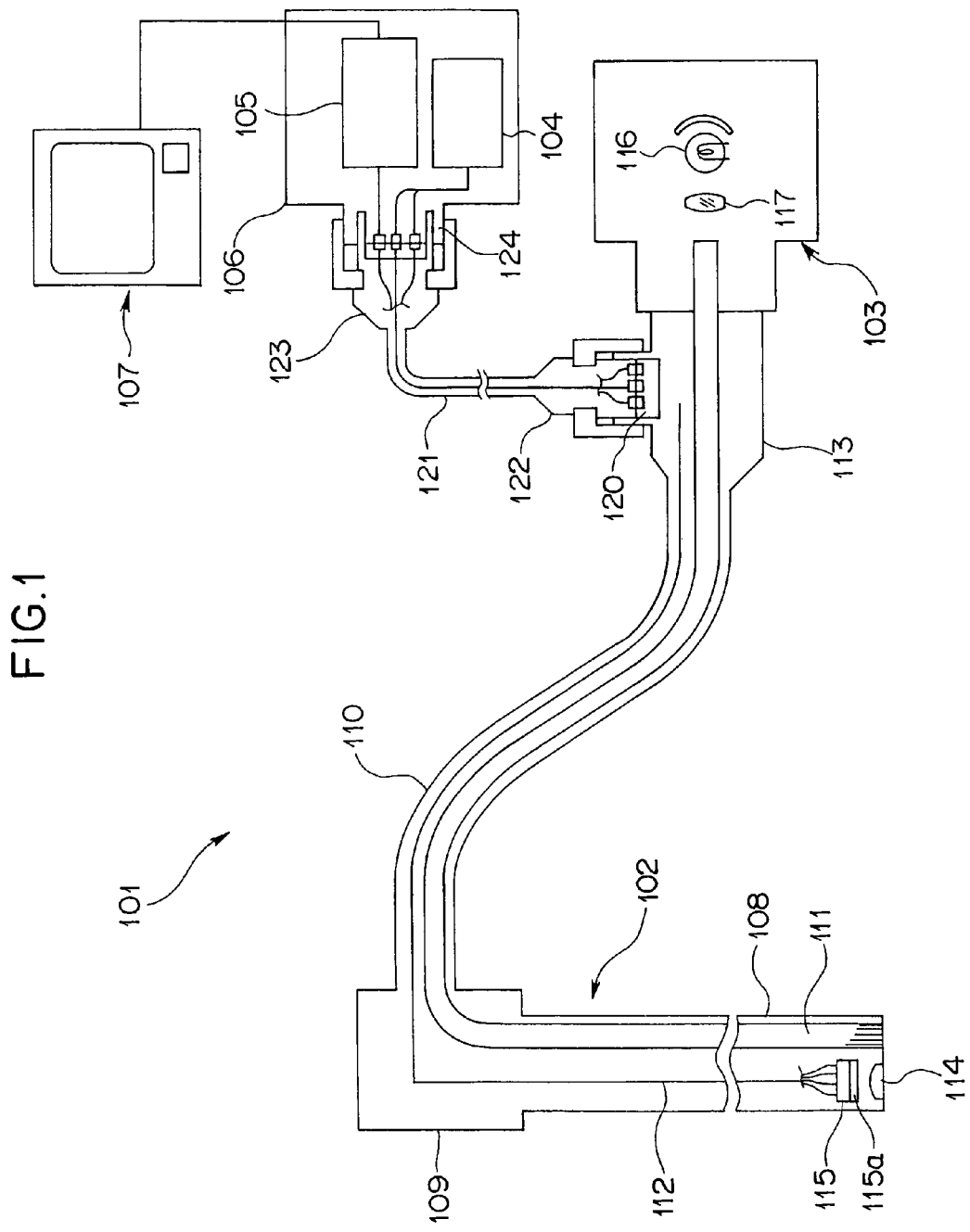
FIG. 1 is a schematic configuration diagram of an electronic endoscope system.
Figure 2:
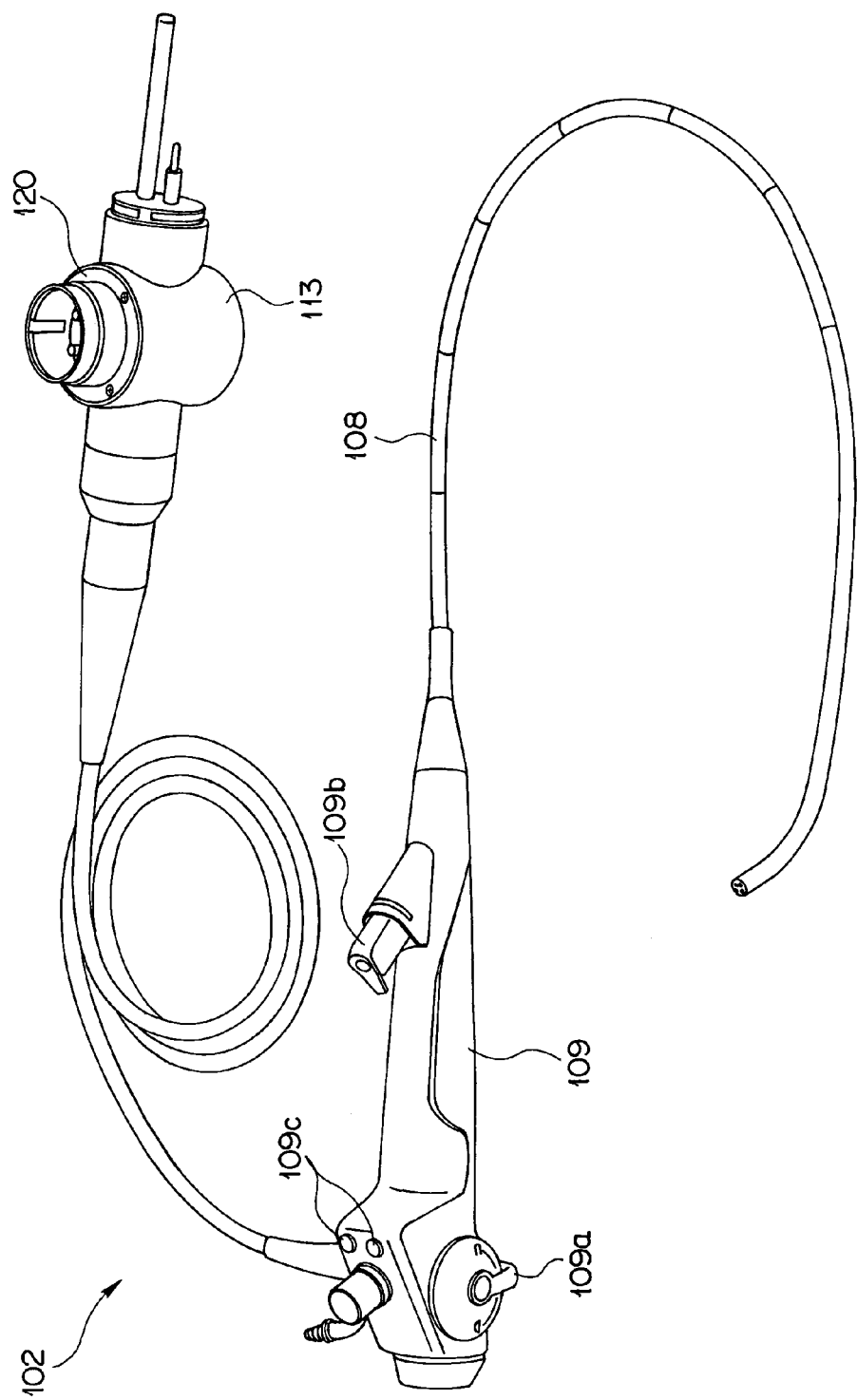
FIG. 2 is an appearance diagram of an electronic endoscope.
Figure 3:
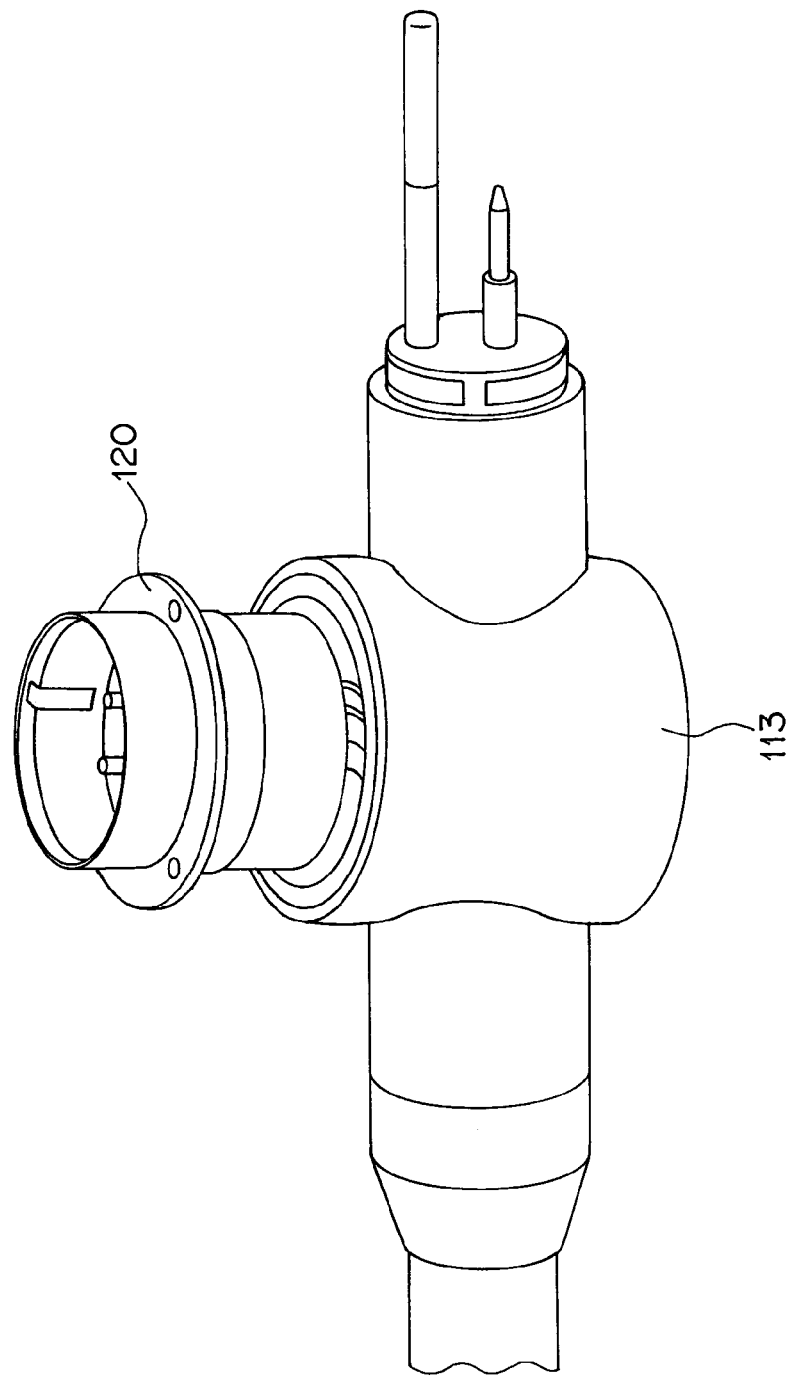
FIG. 3 is an appearance diagram showing a state in which an electric connector is removed from a scope connector.

FIG. 1 is a schematic configuration diagram of an electronic endoscope system. FIG. 2 is an appearance diagram of the electronic endoscope. FIG. 3 is an appearance diagram of a scope connector after an electric connector is removed therefrom.

First of all, a configuration of the electronic endoscope system will be described with reference to FIG. 1. An electronic endoscope system 101 mainly includes an electronic endoscope (which will be simply called endoscope, hereinafter) 102, a light source device 103, a video processor 106 and a monitor 107.

The endoscope 102 shown in FIGS. 1 and 2 includes a long and narrow flexible insertion portion 108, an operation portion 109 and a universal cord 110. The insertion portion 108 is inserted into a body cavity. The operation portion 109 is provided on the proximal side of the insertion portion 108 and is grasped and operated by an operator. The universal cord 110 extends from the operation portion 109 and serves as a connection cable. The insertion portion 108, operation portion 109 and universal cord 110 internally contain a light guide 111 and cable line 112.

One end of the light guide 111 is provided at the distal end of the insertion portion 108 while the other end is connected to the light source device 103 via a scope connector 113 at the proximal end of the universal cord 110. One end of the cable line 112 is connected to an image pickup unit 115 and a switch, which will be described later while the other end is connected to an electric connector 120 in the scope connector 113. The image pickup unit 115 includes a solid image pickup device 115*a* such as a CCD and a CMOS (which is a CCD in this embodiment) at the focal position of an objective lens 114 at the distal end of the insertion portion 108.

As shown in FIG. 2, the insertion portion 109 includes a bending operation knob 109*a*, a treatment tool insertion hole 109*b* and image processing unit switches 109*c* such as a release switch, a freeze switch and an enhance switch. The bending operation knob 109*a* is used for bending/operating a bending portion on the distal side of the insertion portion 108. The treatment tool insertion hole 109*b* is used for inserting a treatment tool into a treatment tool channel within the insertion portion 108. The image processing unit switches 109*c* are used for controlling the driving of the CCD 115*a* of the image pickup unit 115 for an operation on a moving image/still image, for example.

The operation portion 109 includes an air/water feeding button, a suction button, and a front water feeding-button, all of the buttons are not shown. The air/water feeding button is for air/water feeding to the surface of the objective lens 114 (see FIG. 1) at the distal end of the insertion portion 108. The suction button is for suction of a stain and/or water, for example, in a body cavity. The front water feeding button is to feed cleaning water for cleaning the inside of a body cavity. The image processing unit switches 109*c* provided in the operation portion 109 are connected to the video processor 106 via the electric connector 120 in the scope connector 113 of the universal cord 110.

The light source device 103 includes an air/water feeding pump, not shown, for the air/water feeding. A suction pump for suction and a front water feeding pump, not shown, for front water feeding are provided separately from the light source device 103. The endoscope 102 is configured to be capable of implementing air/water feeding, suction and front water feeding functions through these pumps.

Referring back to FIG. 1, the light source device 103 includes a light source lamp 116, a condensing lens 117, a control circuit, not shown, and the air/water feeding pump. The condensing lens 117 concentrates illumination light from the light source lamp 116 and emits it to the input end of the light guide 111 within the scope connector 113. The control circuit turns on and adjusts light of the light source lamp 116.

The video processor 106 is a signal processing unit having a drive circuit 104 and a signal processing circuit 105. The drive circuit 104 controls the driving of the CCD 115*a* at the distal end of the insertion portion 108 of the endoscope 102. The signal processing circuit 105 performs processing on a shot signal optoelectronically converted by the CCD 115*a* of the image pickup unit 115 and generates an endoscope video signal thereby. The light source device 103 and the video processor 106 are integrally provided.

The monitor 107 displays an endoscope image in accordance with a video signal processed by the signal processing circuit 105 of the video processor 106.

As shown in FIGS. 1 and 2, the scope connector 113 at the proximal end of the universal cord 110 has an electric connector 120 which connects the incident end of the light guide 111 to the light source device 103 as described above and connects to the other end of the cable line 112 of the electronic endoscope 102.

The electric connector 120 connects to a removable connection plug 122 at one end of the connection cord 121. The connection cord 121 includes multiple cable lines for connection with the video processor 106, which is an external apparatus used in combination with the electronic endoscope 102.

The other end of the connection cord 121 has a connection plug 123, which is similar to the connection plug 122. The connection plug 123 is removably attached to the electric connector 124 in the video processor 106. The electric connector 124 in the video processor 106 has a substantially similar structure to that of the electric connector 120.

In other words, the electric connector 120 connects to the removable connection plug 122, which allows the electric connection of the ends of the signal lines of the cable line 112 including a signal line for transmission/reception of a CCD drive control signal for connecting the image pickup unit 115 at the distal end of the insertion portion 108 and the video processor 106, a shot signal, driving power and so on, a signal line for supplying a signal from any one of the image processing unit switches 109*c* and a signal line for light adjustment control.

As shown in FIG. 3, the electric connector 120 is fixed to the scope connector 113 with a fixing member in an assembly process and is removable in a maintenance process, for example.

Next, the electric connector 120 will be described with reference to FIGS. 4 to 8.

Figure 4:
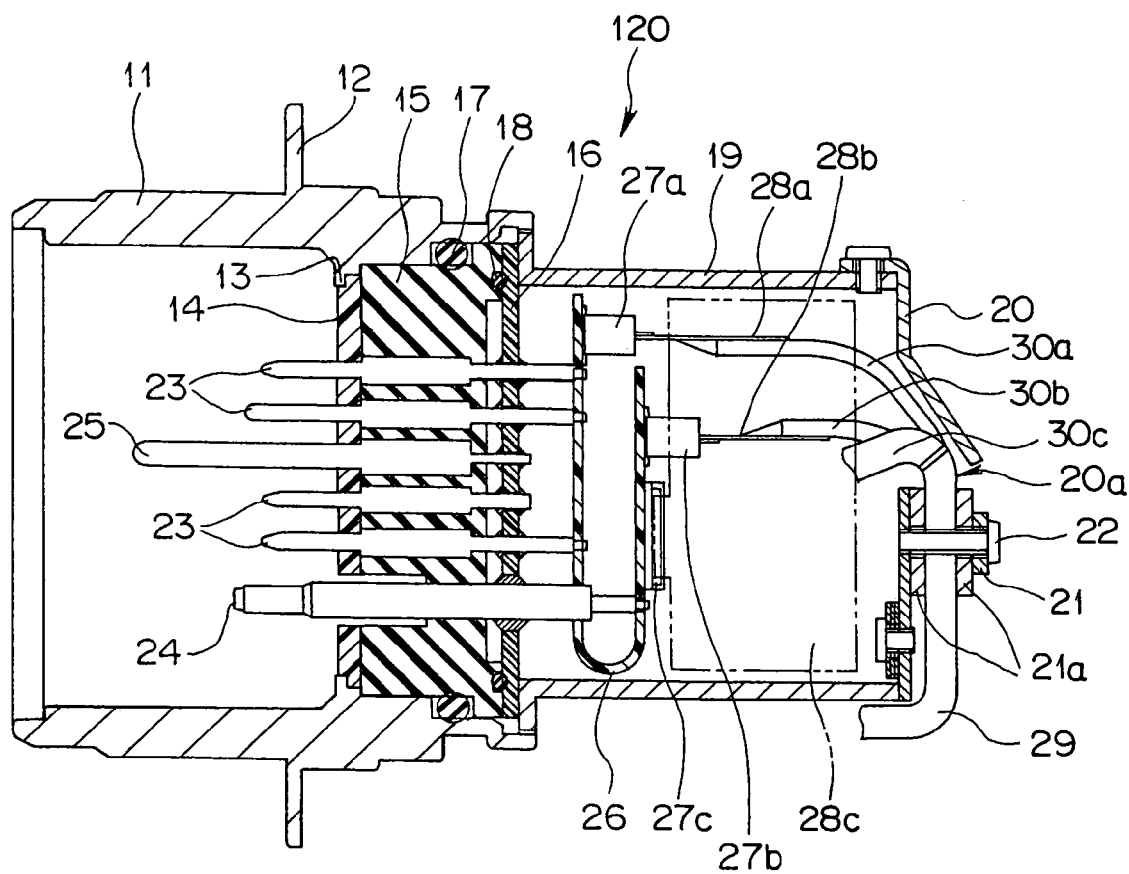
FIG. 4 is a vertical section view showing a structure of the electric connector in the scope connector of the electronic endoscope.
Figure 5:
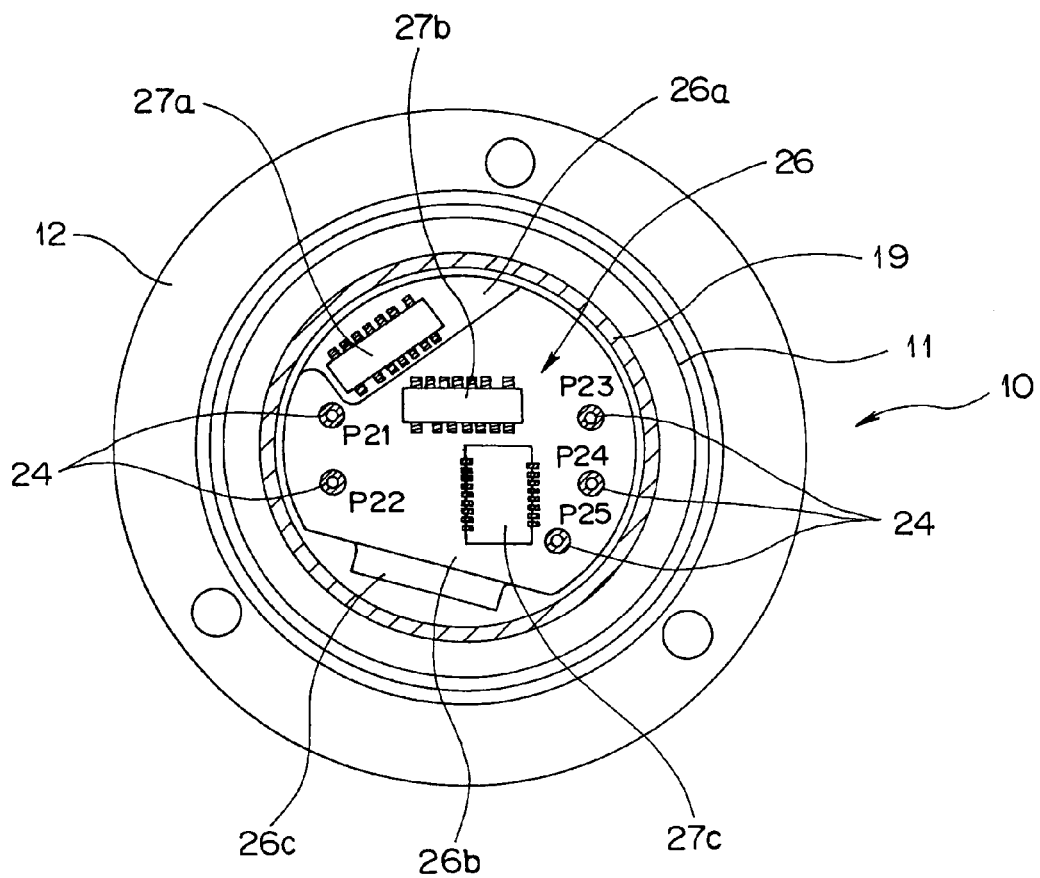
FIG. 5 is a plan view of the electric connector in which a connector substrate is mounted within a shield frame.
Figure 6:
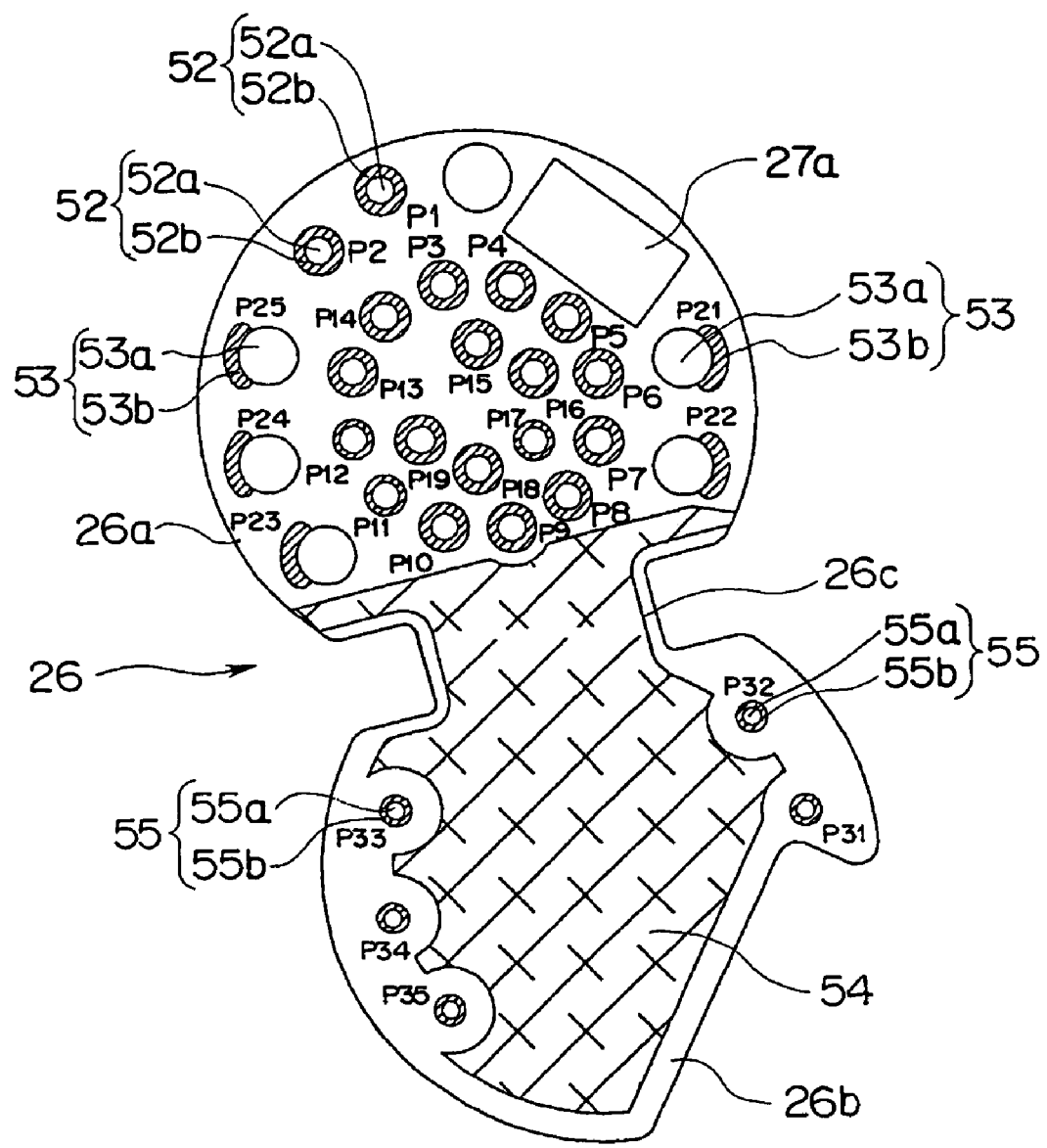
FIG. 6 is a plan view of the front side showing a structure of the connector substrate used in the electric connector of the endoscope.
Figure 7:
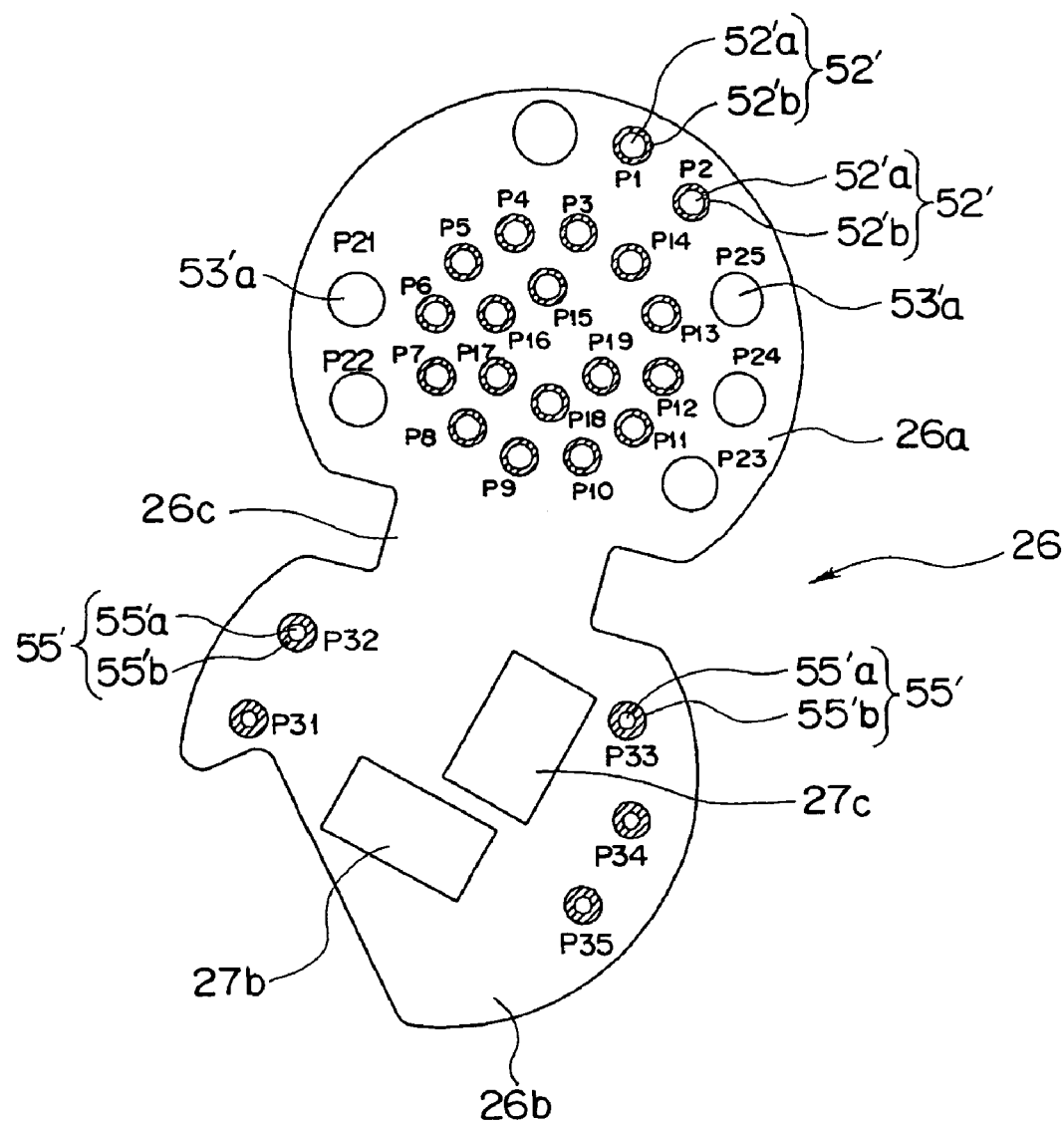
FIG. 7 is a plan view of the back side of the connector substrate shown in FIG. 6.
Figure 8:
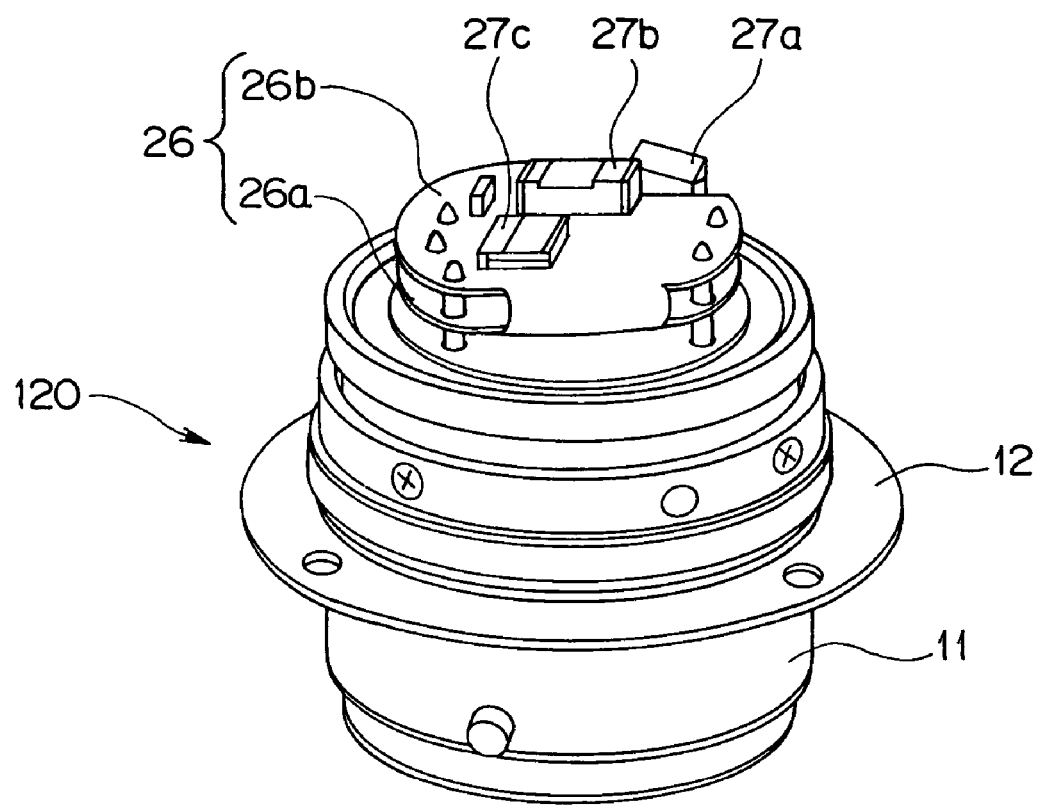
FIG. 8 is an appearance diagram showing a state in which the connector substrate is attached to the electric connector.

FIG. 4 is a vertical section view showing a structure of the electric connector 120 in the scope connector 113 of the electronic endoscope 102. FIG. 5 is a plan view of the electric connector 120 in which a connector substrate is mounted within a shield frame. FIG. 6 is a plan view on the front side showing a structure of the connector substrate used in the electric connector 120 of the endoscope. FIG. 7 is a plan view on the back side of the connector substrate shown in FIG. 6. FIG. 8 is an appearance diagram showing a state in which the connector substrate is attached to the electric connector 120.

As shown in FIG. 4, the electric connector 120 has a cylindrical base 11 to which the electric connector plug 122 at the end of the above-described connection cord 121 is to be connected. The outer periphery of the base 11 has a flange 12 to be attached to the scope connector 113 with a screw, for example.

The rear end side of the inner periphery of the base 11 has an engaging projection 13, and a substantially circular cover member 14 is abutted on the engaging projection 13. An insulator 15 containing an insulating member is disposed on the back face of the cover member 14, and a substrate 16 is disposed on the back face of the insulator 15.

Each of the cover member 14, insulator 15 and substrate 16 is bonded and fixed thereto. The cover member 14, insulator 15 and substrate 16 have a solid-wire pin 23 serving as a solid-wire terminal, a coaxial pin 24 serving as a coaxial terminal and a post pin 25.

A packing 17 for keeping water tightness is provided between the inner periphery of the base 11 and the outer periphery of the insulator 15. A packing 18 for keeping water tightness is provided between the insulator 15 and the vicinity of the outer periphery of the substrate 16.

A cylindrical shield frame 19 is provided on the outer circumferential surface side of the back face of the substrate 16. The distal end of the shield frame 19 is screwed and fixed to the rear end of the base 11 with a fixing member such as a screw, not shown. The shield frame 19 is screwed and fixed to the rear end of the base 11.

Thus, the pattern of the ground potential, not shown, at the outer periphery on the side in contact with the shield frame 19 of the substrate 16 is electrically in contact with the shield frame 19 and connects to the base 11 through the shield frame 19. In other words, the base 11, the ground potential pattern of the substrate 16 and the shield frame 19 have electrical continuity.

A shield lid 20 is attached to the rear end of the shield frame 19 with a fixing member such as a screw. The shield lid 20 includes a shield member having an opening 20a through which a cable line 29 extends. The cable line 29 is fixed therein with a cable line stopping plate 21 internally containing a cushion member 21a fixed with a screw 22.

The cable line 29 includes a scope connector signal line 30a, an operation portion signal line 30b and an insertion portion signal line 30c. The scope connector signal line 30a includes multiple signal lines internally contained in the scope connector 113 for controlling the adjustment of light of the light source device 103 from the video processor 106. The operation portion signal line 30b includes multiple signal lines from the image processing unit switches 109c in the operation portion 109 of the electronic endoscope 102.

The insertion portion signal line 30c includes multiple signal lines from the image pickup unit 115. The scope connector signal line 30a, operation portion signal line 30b and insertion portion signal line 30c are multiple solid wires or coaxial lines.

The distal end of the scope connector signal line 30a of the cable line 29 connects to a cable line connector 28c serving as an endoscope electric connection device including a flexible substrate according to the present invention, which will be described later. The distal ends of the operation portion signal line 30b and insertion portion signal line 30c connect to the connectors 28a and 28b including flexible substrates.

The multiple solid-wire pins 23, multiple coaxial pins 24 and single post pin 25 connect to a substrate 16 through the cover member 14 and insulator 15 on the inner periphery of the base 11. Here, the solid-wire pins 23, coaxial pins 24 and single post pin 25 serve as connection members connecting to the connection plug 122 of the connection cord 121 from a signal processing unit, which is an external apparatus (the video processor 106 in this embodiment). The solid-wire pins 23, coaxial pins 24 and post pin 25 projecting on the distal surface side of the cover member 14 are inserted into pin receivers in the connection plug 122 connecting to the inner periphery of the base 11.

The solid-wire pins 23, coaxial pins 24 and post pin 25 are bonded and fixed to the insulator 15, and the rear ends are held within through-holes in the substrate 16 and are soldered to lands around the through-holes.

The solid-wire pins 23 and coaxial pins 24 soldered to the substrate 16 and extending to the back of the substrate 16 are held within through-holes in the connector substrate 26 and are soldered to lands around the through-holes.

The connector substrate 26 has through-holes and lands and includes micro-connectors 27a to 27c, as described later. The through-holes serve as holes which hold the solid-wire pins 23 and the coaxial pins 24. The lands around the through-holes are to be soldered. The micro-connectors 27a to 27c connect to the cable line connectors 28a to 28c at the distal ends of the scope connector signal line 30a, operation portion signal line 30b and insertion portion signal line 30c, respectively, of the cable line 29. The connector substrate 26 further has a connection pattern for connecting between the lands for the solid-wire pins 23 and coaxial pins 24 and the micro-connectors 27a to 27c.

Next, the connector substrate 26 in the electric connector 120 will be described with reference to FIGS. 5 to 7.

As shown in FIG. 5, the connector substrate 26 having the solid-wire pins 23 (not shown in FIG. 5) and coaxial pins 24 soldered is provided within the shield frame 19 of the electric connector 120. The connector substrate 26 includes one flexible substrate and the three micro-connectors 27a to 27c connecting to the connectors 28a and 28b and cable line connector 28c at the distal ends of the signal lines 30a to 30c, respectively, of the cable line 29.

The connector substrate 26 mainly includes a substantially-circular first substrate portion 26a and a substantially-circular second substrate portion 26b. The first substrate portion 26a connects to the shield portions of the solid-wire pins 23 and coaxial pins 24. The second substrate portion 26b connects to the conductor portions of the coaxial pins 24. The connector substrate 26 has a connection pattern, not shown, for providing electric connection between the first substrate portion 26a and the second substrate portion 26b and further has a bending portion 26c, which is bendable to a substantial-U shape in such a way that the first substrate portion 26a and the second substrate portion 26b can face against each other.

Next, a detail structure of the connector substrate 26 will be described with reference to FIGS. 6 and 7.

As shown in FIG. 6, the back face of the first substrate portion 26a of the connector substrate 26 has multiple solid-wire pin lands 52 and multiple coaxial shield pin lands 53. The solid-wire pin lands 52 have multiple through-holes 52a serving as holes holding the solid-wire pins 23 therein and lands 52b around the through-holes 52a.

The coaxial shield pin lands 53 have multiple through-holes 53a serving as holes holding the shield portions of the coaxial pins 24 therewithin and lands 53b on the outer edge side of the partial periphery of the through-holes 53a.

The multiple solid-wire pin lands 52 are provided at the center of the first substrate portion 26a as indicated by the reference numerals P1 to P19 in FIG. 6. The multiple coaxial shield pin lands 53 are provided on the outer edge side of the first substrate portion 26a with respect to the solid-wire pin lands 52 at the center as indicated by the reference numerals P21 to P25 in FIG. 6.

The first substrate portion 26a further includes the micro-connector 27a to which the connector 28a of the scope connector signal line 30a is attached. The micro-connector 27a is provided on the outer periphery side of the first substrate portion 26a.

The back face of the second substrate portion 26b of the connector substrate 26 has multiple through-holes 55a and coaxial conductor pin lands 55 (indicated by the reference numerals P31 to P35 in FIG. 6) and includes a shield film 54.

The multiple through-holes 55a are holes into which the conductor portions of the coaxial pins 24 at the corresponding positions are inserted into the respective multiple coaxial shield pin lands 53 (indicated by the reference numerals P21 to P25 in FIG. 6) on the first substrate portion 26a when the connector substrate 26 is bent about the bending portion 26c such that the second substrate portion 26b can face to the first substrate portion 26a.

The coaxial conductor pin lands 55 (indicated by the reference numerals P31 to P35 in FIG. 6) have the multiple through-holes 55a and lands 55b around the through-holes 55a. The shield film 54 is on the entire area of the back face of the second substrate portion 26b excluding the coaxial conductor pin lands 55.

The shield film 54 is mainly provided for the purpose of electromagnetic shield between the first substrate portion 26a and the second substrate portion 26b and extends from the bending portion 26c to a part of the first substrate portion 26a and electrically connects to the ground potential pattern, not shown.

On the other hand, the front face of the first substrate portion 26a of the connector substrate 26 has multiple holes 52'a, multiple solid-wire pin lands 52' (indicated by the reference numerals P1 to P19 in FIG. 7) and multiple holes 53'a (indicated by the reference numerals P21 to P25 in FIG. 7).

The multiple holes 52'a communicate to the through-holes 52a of the multiple solid-wire pin lands 52 (indicated by the reference numerals P1 to P19 in FIG. 6) on the back face of the first substrate portion 26a. The multiple solid-wire pin lands 52' have the multiple holes 52'a and lands 52'b around the multiple holes 52'a.

The multiple holes 53'a (indicated by the reference numerals P21 to P25 in FIG. 7) communicate to the through-holes 53a of the multiple coaxial shield pin lands 53 (indicated by the reference numerals P21 to P25 in FIG. 6), respectively, on the back face of the first substrate portion 26a.

The second substrate portion 26b has multiple coaxial conductor pin lands 55' (indicated by the reference numerals P31 to P35 in FIG. 7) comprising multiple holes 55'a and lands 55'b around the holes 55'a. The holes 55'a communicate to the through-holes 55a of the multiple coaxial conductor pin lands 55 (indicated by the reference numerals P31 to P35 in FIG. 6), respectively, on the back face.

Micro-connectors 27b and 27c are mounted substantially at the center of the front face of the second substrate portion 26b. The cable line connector 28b of the operation portion signal line 30b of the cable line 29 is attached to the micro-connector 27b. The cable line connector 28c of the insertion portion signal line 30c is attached to the micro-connector 27c.

Notably, the second substrate portion 26b has a notch at a part lying on the micro-connector 27a on the first substrate portion 26a when the second substrate portion 26b is laid on the first substrate portion 26a. The notch in the second substrate portion 26b allows easy attachment of the connector 28a to the micro-connector 27a mounted on the first substrate portion 26a.

In other words, when the connector substrate 26 being a flexible substrate is bent about the bending portion 26c such that the first substrate portion 26a and the second substrate portion 26b can be laid one over another, the connecting members such as the solid-wire pins 23 and coaxial pins 24 to mainly connect to an external apparatus connect to one surface of the front face of the first substrate portion 26a and the back face of the second substrate portion 26b.

Furthermore, the micro-connectors 27a, 27b and 27c are mounted on the other surface of the back face of the first substrate portion 26a and front face of the second substrate portion 26b of the connector substrate 26. The connectors 28a and 28b of the cable line 29 contained in the universal cord 11 of the electronic endoscope and the cable line connector 28c are mainly attached to the micro-connectors 27a, 27b and 27c, respectively.

The micro-connectors 27a to 27c are connected via the respective solid-wire pin lands 52 (indicated by the reference numerals P1 to P19 in FIG. 7), coaxial shield pin lands 53 (indicated by the reference numerals P21 to P25 in FIG. 7), coaxial conductor pin lands 53 (indicated by the reference numerals P31 to P35 in FIG. 7) and the connection pattern, not shown.

Notably, in this embodiment, the numbers of the multiple solid-wire pin lands 52, multiple coaxial shield lands 53 and multiple coaxial conductor pin lands 55 and the number of the micro-connecters 27a to 27c are used for the illustrative purpose only, and the types, thickness and numbers of the signal lines 30a to 30c included in the cable line 29 and the number of poles of the micro-connectors 27 may be changed.

The connector substrate 26 arranged as described above is attached to the electric connector 120 such that the first substrate portion 26a and the back face of the second substrate portion 26b can face each other as shown in FIG. 8. Here, the multiple solid-wire pins 23 are soldered to the substrate 16 at the middle and is electrically connected to the substrate 16 as shown in FIG. 4. The solid-wire pins 23 further maintain the positional relationship between the insulator 15 and the substrate 16.

Some of the multiple solid-wire pins 23 are short in the axial direction, and the short solid-wire pins 23 are mainly used for the electrical connection and positional maintenance with the substrate 16. The ends on the proximal side of the short solid-wire pins 23 are inserted into through-holes in the substrate 16 and are soldered to the lands around the through-holes in the both sides of the substrate 16.

Thus, according to this embodiment, the substrate 16 and the short solid-wire pins 23 are electrically connected. The substrate 16 further includes a connection pattern with an electronic part mounted on the substrate 16 and a ground potential pattern. The multiple short solid-wire pins 23 are electrically connected to the connection pattern or ground potential pattern through the soldered lands.

The ends on the proximal side of the multiple solid-wire pins 23, which are different from the short solid-wire pins 23, are inserted into the through-holes 52a of the solid-wire pin lands 52 of the first substrate portion 26a of the connector substrate 26 (see FIGS. 6 and 7) and are soldered to the lands 52b around the through-holes 52a. Thus, the substrate 16 and the first substrate portion 26a of the connector substrate 26 are electrically connected.

The ends on the proximal side of the multiple coaxial pins 24 are inserted into the through-holes 55a of the coaxial conductor pin lands 55 of the second substrate portion 26b of the connector substrate 26 (see FIGS. 6 and 7) and are soldered to the lands 55b around the through-holes 55a. Thus, the first substrate portion 26a and second substrate portion 26b of the connector substrate 26 are held with a predetermined space therebetween and are electrically connected.

The ends on the proximal sides of the outer periphery, which serve as a shield, of the multiple coaxial pins 24 are inserted into the through-holes 53a of the coaxial pin lands 53 on the first substrate portion 26a of the connector L substrate 26 (see FIGS. 6 and 7) and are soldered to the coaxial shield pin lands 53 of the first substrate portion 26a. The post pin 25 is inserted into a through-hole in the substrate 16 and is soldered to the land around the through-hole on both sides of the substrate 16.

Thus, the facing surfaces of the substrate 16 and the first substrate portion 26a and second substrate portion 26b of the connector substrate 26 are spaced by predetermined distances, mechanically held and electrically connected through the solid-wire pins 23 and coaxial pins 24 in the cover member 14 and insulator 15 within the base 11.

The cable line connector 28c, which is an endoscope electric connection device of the invention according to this embodiment, will be described in detail with reference to FIGS. 9 to 13.

Figure 9:
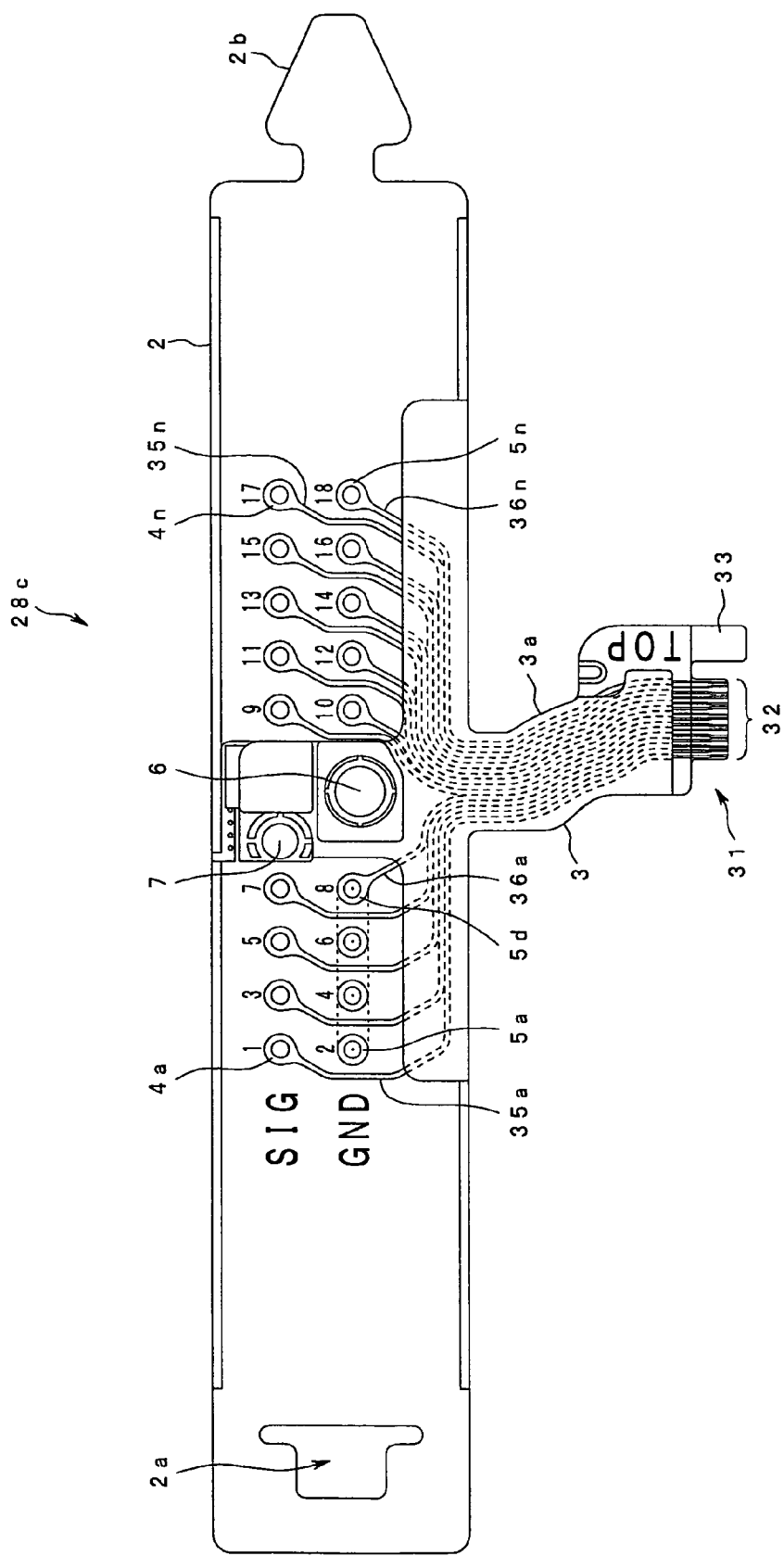
FIG. 9 is a plan view showing a cable line connector 28c of the present invention.
Figure 10:
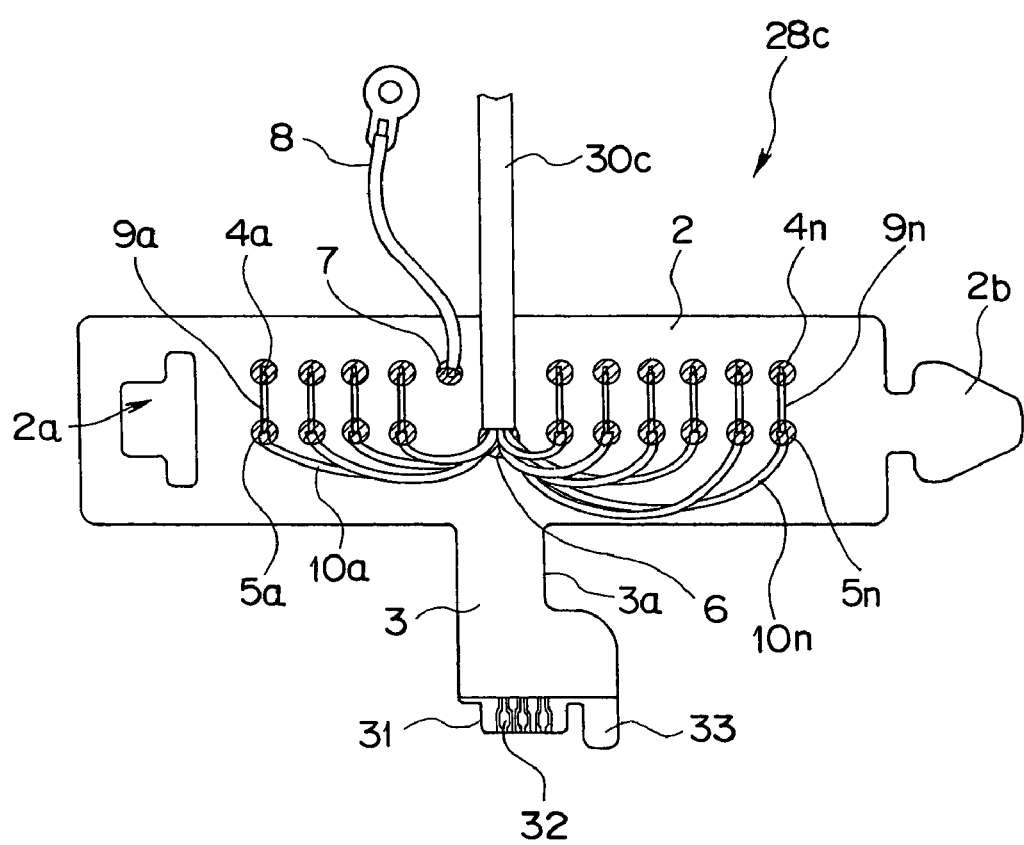
FIG. 10 is a plan view of the cable line connector 28c to which an insertion portion signal cable is connected.
Figure 11:
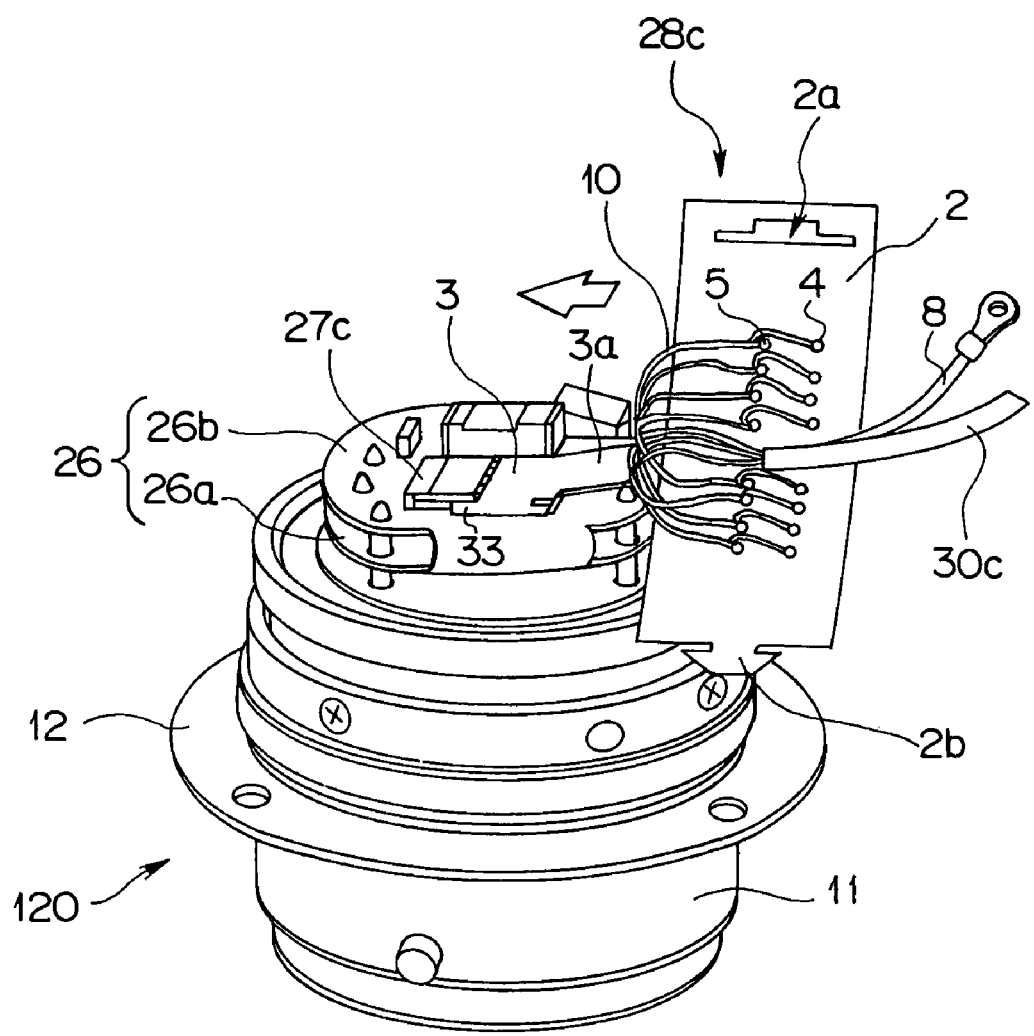
FIG. 11 is an operation explanatory diagram showing a state in which the cable line connector of the present invention is mounted to the connector substrate of the electric connector.
Figure 12:
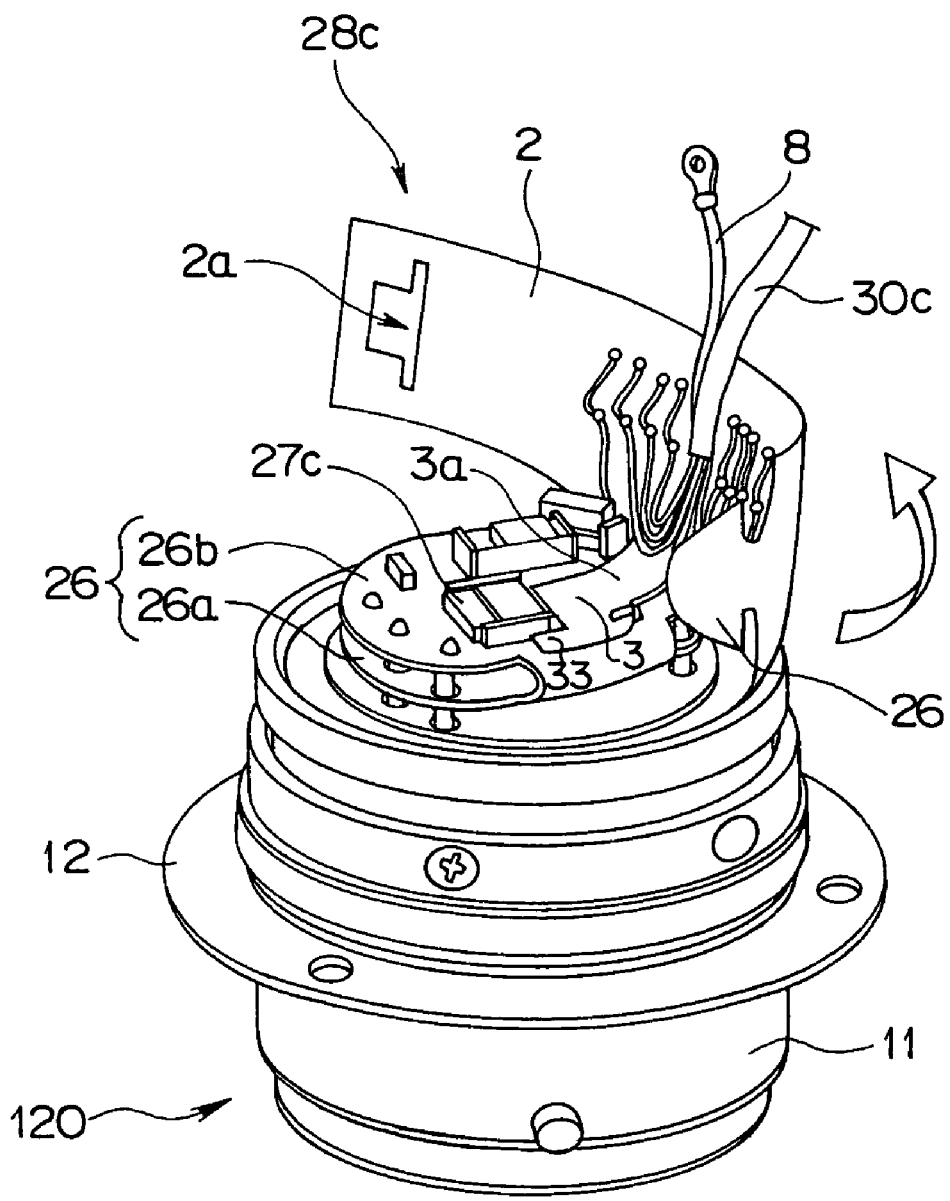
FIG. 12 is the operation explanatory diagram showing another state in which the cable line connector of the present invention is mounted to the connector substrate of the electric connector.
Figure 13:
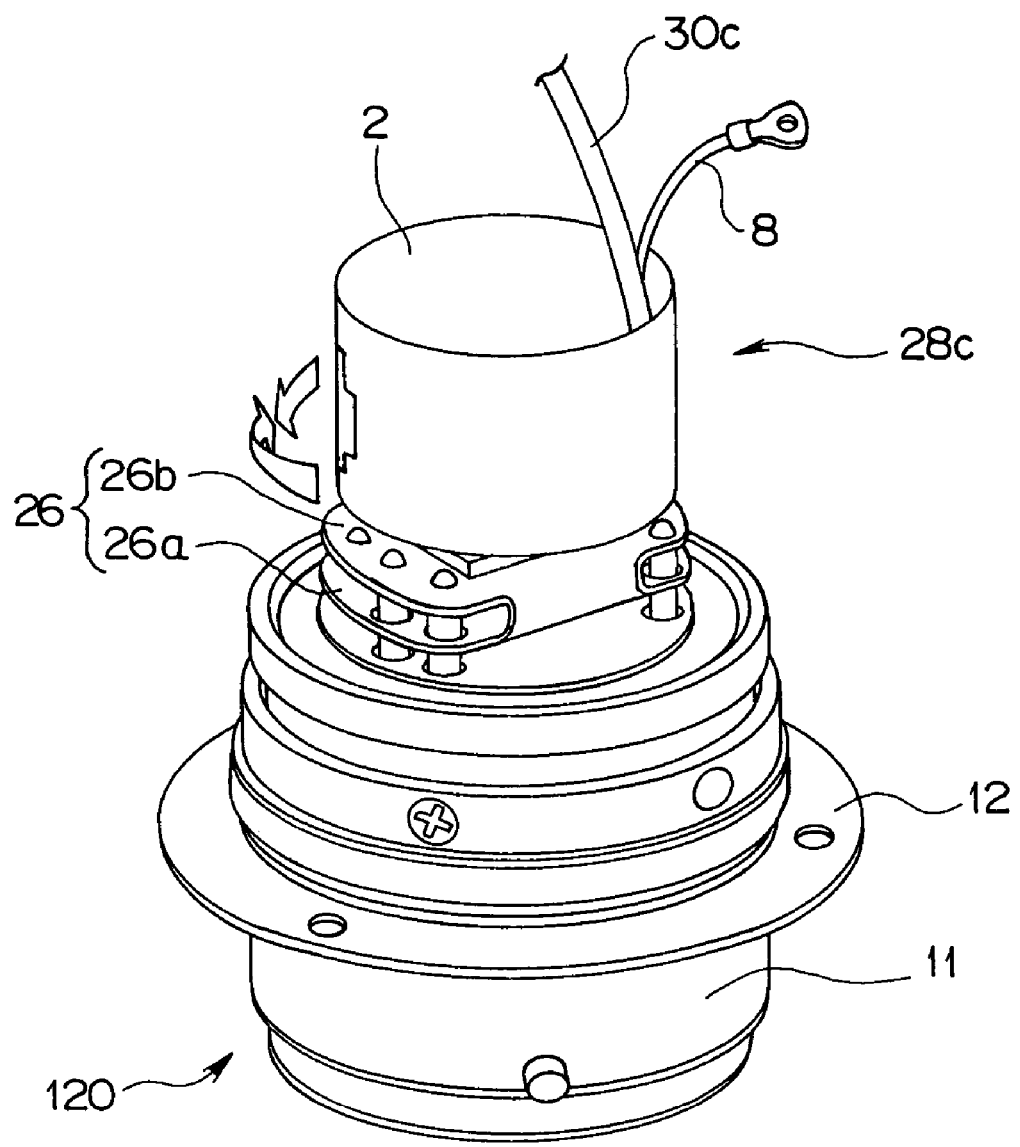
FIG. 13 is the operation explanatory diagram showing another state in which the cable line connector of the present invention is mounted to the connector substrate of the electric connector.

FIG. 9 is a plan view showing the cable line connector 28c. FIG. 10 is a plan view of the cable line connector 28c to which a composite cable is connected. FIGS. 11 to 13 are operation explanatory diagrams each showing a state in which the cable line connector 28c is mounted to the connector substrate 26 of the electric connector 120.

As shown in FIGS. 9 and 10, the cable line connector 28c, which is an endoscope electric connection device, includes a cable line connecting portion 2 serving as a first band part and a connection terminal portion 3 serving as a second band part. The cable line connecting portion 2 is slightly wide rectangular and flexible first contact placing means. The connection terminal portion 3 is flexible second contact placing means extending from the side of the substantial center of the cable line connecting portion 2. The cable line connector 28c is a flexible substrate substantially having a T-shape as a whole.

One surface of the cable line connecting portion 2 two-dimensionally has multiple signal lands 4 (4a to 4n) serving as a first contact portion and multiple ground lands 5 (5a to 5n) serving as a second contact portion. The multiple signal lands 4 and the multiple ground lands 5 are used for connecting multiple electric wires substantially-equally spaced in longitudinal two lines. The cable line connecting portion 2 has a wider area than that of the connection terminal portion 3 for easy connection of the multiple electric wires.

The multiple signal lines 4 (4a to 4n) are aligned in one line at the upper part of the cable line connecting portion 2 in FIG. 9. On the other hand, the multiple ground lands 5 (5a to 5n) are aligned in one line at the lower part of the cable connecting portion 2 in FIG. 9.

The multiple signal lands 4 (4a to 4n) and ground lands 5 (5a to 5n) are spaced for easy soldering connection in accordance with the type, thickness and so on of the connected coaxial lines.

The substantial center of the cable line connecting portion 2 has a ground land 6 and a lead line land 7. A total ground shield serving as a ground line of the insertion portion signal line 30c is soldered to the ground land 6. The lead line land 7 is electrically continuous with the ground land 6. One end of a ground lead line 8 is connected to the lead line land 7 by soldering.

The ground lead line 8 has a ring-shaped connecting portion at the other end, and the connecting portion is connected to the ground potential of the electric connector 10.

The connection terminal portion 3 serving as the second electric connecting portion as described above has a deformation part 3a and a terminal portion 31. The deformation part 3a extends from the vicinity of the center of the side of the cable line connecting portion 2. The terminal portion 31 serves as a third contact portion for electrical connection at one end, which is an extension end of the deformation part 3a. The terminal portion 31 has multiple terminal pieces 32 and has a form to be plugged in the micro-connector 27c on the connector substrate 26.

The terminal portion 31 includes a guide piece 33 serving as a guide portion extending in parallel with the longitudinal direction of the multiple terminal pieces 32. The guide piece 33 is narrower than the width of the part having the multiple terminal pieces 32 and is attached to a guide piece plug, not shown, which is provided together with the plug, not shown, of the micro-connector 27. Then, the guide piece 33 is fixed to the micro-connector 27 by bonding or soldering, for example.

Thus, the terminal portion 31 can prevent an upside-down insertion error upon plug in the micro-connector 27c. Notably, the micro-connector 27 may have a guided part such as a guide groove such that the guide piece can be attached along one side of the cabinet.

The signal lands 4 (4a to 4n) and ground lands 5 (5a to 5n) are electrically connected to the corresponding terminal pieces 32 of the terminal portion 31 through the connection patterns 35 (35a to 35n) and 36 (36a to 36n). The connection patterns 35 (35a to 35n) and 36 (36a to 36n) are included in a transmitting portion, which is transmitting means in the cable line connector 28c of this embodiment.

Furthermore, the left four ground lands 5a to 5d with respect to the ground land 6 in FIG. 9 are electrically connected to the cable line connector 28c of this embodiment at the back, and the ground land 5d is electrically connected to one of the multiple terminal pieces 32 through the connection pattern 36a.

The cable line connector 28c further has a convex-shaped cut hole 2a in one end part of the cable line connecting portion 2 and a hook-like part 2b in the other end part. The hook-like part 2b substantially has an isosceles triangular form projecting in the longitudinal direction and has a connection piece having a predetermined width at the base of the triangular form.

Thus, in order to keep the cable line connecting portion 2 of the cable line connector 28c of the present invention in a substantially cylindrical form, the isosceles triangular form of the hook-like part 2b is inserted to the wider part of the convex-shaped cut hole 2a, and the connection piece of the hook-shaped part 2b is attached to the narrower part of the convex-shaped cut hole 2a.

The multiple coaxial lines 10 (10a to 10n) extending within the insertion portion signal line 30c of the cable line 29 are two-dimensionally soldered to the respective multiple signal lands 4 (4a to 4n) and ground lands 5 (5a to 5n). In other words, conductors 9 (9a to 9n) serving as internal conductors and signal lines of the coaxial lines 10 (10a to 10n) of the insertion portion signal line 30c are soldered to the respective corresponding connection lands 4 (4a to 4n). Furthermore, the ground shield of the coaxial lines 10 (10a to 10n) are soldered to the respective connection lands 5 (5a to 5n).

Here, as shown in FIG. 10, the cable line connector 28c of the invention is connected such that the insertion portion signal line 30c can extend toward the opposite side of the side where the connection terminal portion 3 extends, that is, to the upper part in FIG. 10. In other words, since the connection terminal portion 3 connects to the micro-connector 27c on the connector substrate 26 of the electric connector 120, the insertion portion signal line 30c is connected so as to extend from the side of the cable line connecting portion 2 of the cable line connector 28c on the opposite side of the connection terminal portion 3 in consideration of the attachability to the scope connector 113 of the electric connector 120.

The connection between the insertion portion signal line 30c and the cable line connector 28c is kept since the insertion portion signal line 30c is connected by soldering to the ground land 6 of the cable line connector 28 to which the internal total ground shield is soldered. Accordingly, the strength of the connection between the insertion portion signal line 30c and the cable line connector 28c is improved by adopting a thicker and more robust total ground shield to solder to the ground land 6. Therefore, the ground land 6 is disposed substantially at the center of the cable line connecting portion 2 of the cable line connector 28c so that the ground land 6 can be defined in an area as wide as possible.

Furthermore, since the size of the cable line connector 28c depends on the size of the electric connector 120 and scope connector 113, the area of the cable line connecting portion 2 is limited. Therefore, the multiple signal lands 4 (4a to 4n) and ground lands 5 (5a to 5n) must be disposed within a space in the cable line connecting portion 2 efficiently and in consideration of the connectivity of the multiple coaxial lines 10 (10a to 10n) of the insertion portion signal line 30c to be soldered and connected thereto.

For these reasons, in the cable line connecting portion 2 in the cable line connector 28c of the present invention, the multiple signal lands 4 (4a to 4n) are disposed in one line on the side where the insertion portion signal line 30c extends, and the multiple ground lands 5 (5a to 5n) are disposed in one line on the side where the connection terminal portion 3 extends. In other words, the multiple signal lands 4 (4a to 4n) are disposed in one line in the cable line connecting portion 2 to the upper long side in FIG. 9, and the multiple ground lands 5 (5a to 5n) are disposed in one line in the cable line connecting portion 2 to the lower long side in FIG. 9.

Furthermore, the respectively paired multiple signal lands 4 (4a to 4n) and multiple ground lands 5 (5a to 5n) are disposed substantially vertically. In other words, for example, the signal land 4a and ground land 5a are disposed substantially vertically to the upper and lower short sides of the cable line connecting portion 2 so that the conductor 9a of the coaxial line 10 and the ground shield can be connected by soldering and one coaxial line 10 can be thus substantially straight.

Therefore, as shown in FIG. 10, the ground shield of the insertion portion signal line 30c is connected to the ground land 6 by soldering, and the multiple coaxial lines 10 (10a to 10n) extending downward in FIG. 10 are bent upward. Then, the conductors 9 (9a to 9n) are connected to the respective corresponding signal lands 4 (4a to 4n) by soldering, and the ground shields are connected to the respective corresponding ground lands 5 (5a to 5n) by soldering. As a result, the coaxial lines 10 (10a to 10n) do not break easily since, even when pulling force is applied to the insertion portion signal line 30c, the force is not directly applied to the coaxial lines 10 (10a to 10n).

The insertion portion signal line 30c constituted as described above is connected to the cable line connector 28c of the present invention. Next, a state in which the cable line connector 28c is connected to the micro-connector 27c on the connector substrate 26 mounted on the electric connector 120 will be described with reference to FIGS. 11 to 13.

As shown in FIG. 11, the cable line connector 28c connects to the micro-connector 27c with the surface up on which the coaxial lines 10 in the insertion portion signal line 30c are connected to the respective corresponding signal lands 4 and ground lands 5 by soldering.

Here, in the cable line connector portion 28c, the terminal pieces 32 (not shown in FIG. 11) of the terminal portion 31 of the connection terminal portion 3 are plugged in the micro-connector 27c. Furthermore, in the cable line connector portion 28c, the guide piece 33 of the terminal portion 31 is plugged in the guide piece opening in a predetermined manner so that the upside-down insertion error can be prevented and the terminal pieces 32 of the terminal portion 31 can be easily electrically connected to the micro-connector 27c.

Next, as shown in FIG. 12, in the cable line connector 28c, the deformation part 3a of the connection terminal portion 3 is bent to stand the cable line connecting portion 2. Then, in the cable line connector 28c, the triangular hook-like part 2b of the cable connecting portion 2 is inserted into the wide part of the convex-shaped cut hole 2a, and the connection piece of the hook-like part 2b is attached to the narrow part of the convex-shaped cut hole 2a.

Thus, as shown in FIG. 13, the cylindrically bent cable line connector 28c can be kept with the surface inside on which the coaxial lines 10 of the cable line connecting portion 2 are connected. The cable line connector 28c under this condition is accommodated within the shield frame 19 with the shield frame 19 attached to the electric connector 120 as shown in FIG. 4.

Furthermore, the multiple signal lands 4 (4a to 4n) and multiple ground lands 5 (5a to 5n) are electrically connected through the connection patterns 35 (35a to 35n) and 36 (36a to 36n) even when the cable line connecting portion 2 and connection terminal portion 3 are bent.

Notably, in the cable line connector 28c of this embodiment, the connection terminal portion 3 is bent in a first direction along the direction of the short side of the cable line connecting portion 2, and the cable line connecting portion 2 is bent in a second direction along the direction of the long side of the cable line connecting portion 2. In other words, the connection terminal portion 3 and cable line connecting portion 2 are bent in different directions, and the different directions are substantially orthogonal.

As described above, the cable line connector 28 of the invention has a substantially T-shaped flexible substrate and includes the multiple signal lands 4 (4a to 4n) and multiple ground lands 5 (5a to 5n) each in one line at the upper and lower areas along the longitudinal axis of the cable line connecting portion 2 having a horizontally-oriented, planer and rectangular form. The lands 4 and 5 are spaced for easy soldering of the coaxial lines 10 of the insertion portion signal line 30c. The cable line connector 28c further includes the terminal portion 31 having the narrower multiple terminal pieces 32 in the connection terminal portion 3 connecting to the lands 4 and 5 in the cable line connecting portion 2 through the connection patterns 35 (35a to 35n) and 36 (36a to 36n).

Hence, the workability for soldering can be improved in the cable line connector 28c of the invention since the coaxial lines 10 of the insertion portion signal line 30c can be two-dimensionally soldered to the cable line connecting portion 2. Thus, the terminal portion 31 having the multiple terminal pieces 32 can be easily connected to the micro-connector 27c mounted on the connector substrate 26 of the electric connector 120. Furthermore, the cable line connector 28c can be accommodated within the shield frame 19 having a limited space with the deformation part 3a of the connection terminal portion 3 bent and stood and with the cable line connecting portion 2 bent substantially cylindrically.

Therefore, an assembly staff can easily accommodate the electric connector 120 within the scope connector 113. Then, when a failure such as poor contact occurs in the connection between the coaxial lines 10 of the insertion portion signal line 30c and the cable line connector 28c, for example, a repair individual may remove the electric connector 120 from the scope connector 113, pull out the hook-like part 2b of the cable line connector 28c from the cut hole 2a and spread the cable line connector 28c from the substantially cylindrical form in order to check the connection state with the coaxial lines 10 easily.

The repair individual can further easily perform electrical maintenance and repair by connecting the coaxial line 10 having poor contact by soldering again or replacing the cable line connector 28c itself.

In the cable line connecting portion 2, the multiple signal lands 4 are disposed in one line on one longitudinal side in accordance with the direction of the bend of the coaxial lines 10, and the multiple ground lands 5 are disposed in one line on the other longitudinal side. In this case, the corresponding signal lands 4 and ground lands 5 are disposed to be substantially orthogonal to the longitudinal direction. Thus, the conductors 9 and ground shields of the coaxial lines 10 can be easily connected by soldering to the corresponding signal lands 4 and ground lands 5.

The cable line connector 28c of the invention may be configured to have various features as shown in FIGS. 14 to 20, as described below. FIGS. 14 to 20 are plan views showing variation examples of the cable line connector 28c of the invention.

Figure 14:
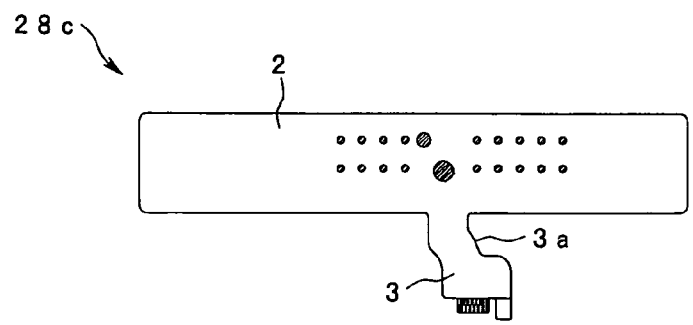
FIG. 14 is a plan view showing a first variation example of the cable line connector of the present invention.

First of all, as shown in FIG. 14, a cable line connector 28c according to a first variation example does not have the convex-shaped cut hole 2a and triangular hook-like part 2b at both ends of the cable line connecting portion 2.

In the cable line connector 28c, like the one described above, the terminal pieces 32 of the connection terminal portion 3 are electrically connected to the connector substrate 26 of the electric connector 120 through the micro-connector 27c, and the cable line connecting portion 2 is then bent to a substantial cylindrical form. Here, the cable line connecting portion 2 of the cable line connector 28c is fixed with a bonding tape or a band, for example, to bring the both ends one over another and is held in a substantial cylindrical form.

Even with this arrangement, the cable line connector 28c under this condition can be accommodated within the shield frame 19 of the electric connector 120.

Figure 15:
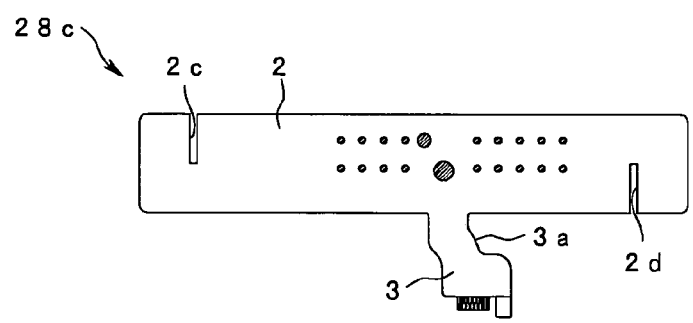
FIG. 15 is a plan view showing a second variation example of the cable line connector of the present invention.
Figure 16:
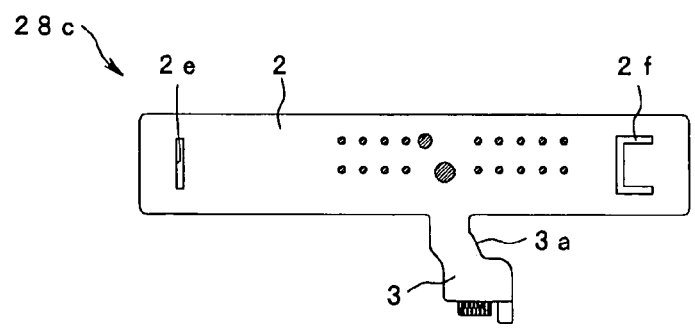
FIG. 16 is a plan view showing a third variation example of the cable line connector of the present invention.
Figure 17:
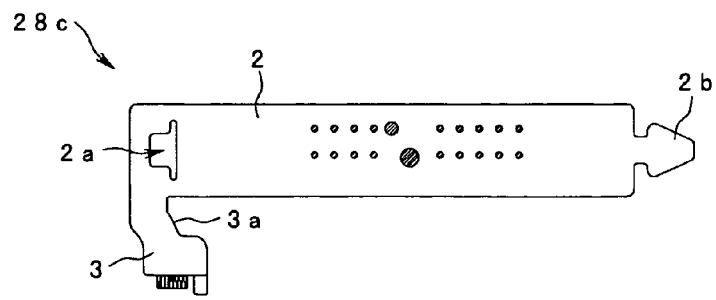
FIG. 17 is a plan view showing a fourth variation example of the cable line connector of the present invention.
Figure 18:
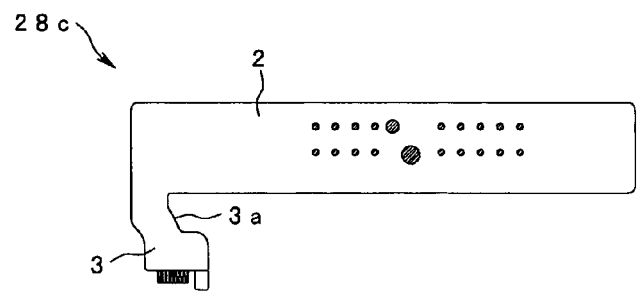
FIG. 18 is a plan view showing a fifth variation example of the cable line connector of the present invention.
Figure 19:
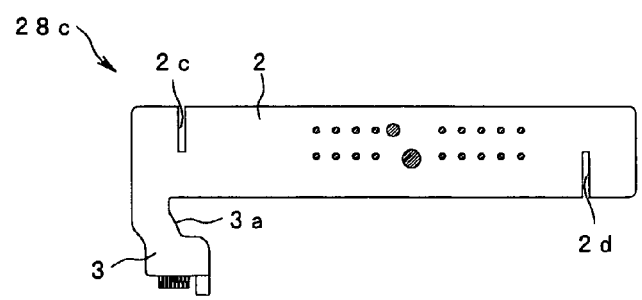
FIG. 19 is a plan view showing a sixth variation example of the cable line connector of the present invention.
Figure 20:
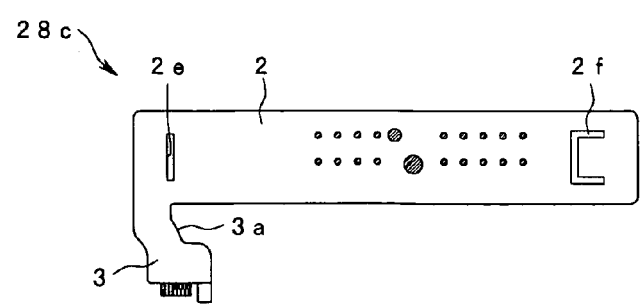
FIG. 20 is a plan view showing a seventh variation example of the cable line connector of the present invention.

Next, as shown in FIGS. 15 and 16, a cable line connector 28c according to second and third variation examples has cuts on both ends of the cable line connecting portion 2 so as to keep the cable line connecting portion 2 in a substantially cylindrical form instead of the convex-shaped cut hole 2a and triangular hook-like part 2b on both ends of the cable line connecting portion 2.

The cable line connector 28c in the second variation example shown in FIG. 15 has cut grooves 2c and 2d in the direction substantially orthogonal to the longitudinal direction on both ends of the cable line connecting portion 2. The cut grooves 2c and 2d extend substantially to the center of the cable line connecting portion 2.

The cut end of one cut groove 2c starts from one side of the cable line connecting portion 2 while the cut end of the other cut groove 2d starts from the other side of the cable line connecting portion 2. Thus, the cable line connecting portion 2 is kept in a substantially cylindrical form by associating the cuts 2c and 2d on both ends from the cut ends of the cut grooves 2c and 2d on both ends.

The cable line connector 28c according to the third variation example shown in FIG. 16 has an I-shaped cut groove 2e in the direction substantially orthogonal to the longitudinal direction substantially at the center of one end of the cable line connecting portion 2 and further has a c-shaped cut groove 2f in FIG. 16 substantially at the center of the other end of the cable line connecting portion 2.

Thus, the cable line connecting portion 2 can be held in a substantially cylindrical form by associating the c-shaped cut groove 2f here at one end into the I-shaped cut groove 2e at the other end.

Notably, in a cable line connector 28c according to fourth and seventh variation examples, a connection terminal portion 3, which extends from one side substantially at the center of the cable line connector 28c according to the embodiment and first and third variation examples, extends one end side of the cable line connecting portion 2 in the direction substantially orthogonal to the longitudinal direction.

In other words, the cable line connector 28c is not functionally damaged even when the position where the connection terminal portion 3 extends is changed on one side of the cable line connecting portion 2.

The cable line connector 28c according to the embodiment of the invention and variation examples may adopt an external apparatus including the video processor 106 serving as a signal processing device and the light source device 103 integrally instead of the external apparatus having the video processor 106 serving as a signal processing device and the light source device 103 separately as described in the example above.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope electric connection device accommodated within a scope connector for connecting an electronic endoscope and an external apparatus, the device comprising:
a first band part having a first contact portion to which a signal line of a transmission cable for transmitting an image signal from an image pickup unit of the electronic endoscope is connected and a second contact portion to which a ground line of the transmission cable is connected, and first band part having flexibility;
a fixing portion comprising:
a convex-shaped hole portion disposed at one end part of the first band part and having a wide part and a narrow part; and
a hook-like part having a triangular form, formed so as to protrude from another end part of the first band part, and having a connection piece having a predetermined width at a base of the triangular form, wherein the bent state of the first band part is kept by the hook-like part being inserted into the width part of the hole portion thus engaging the connection piece with the narrow part;
a second band part having a third contact portion connecting to a connector for electrically connecting to the external apparatus and having flexibility; and
a transmitting portion provided in the first band part and second band part for electrically connecting the first contact portion and second contact portion to the third contact portion,
wherein the transmitting portion can keep electric connection between the first contact portion and second contact portion and the third contact portion even with the first band part and the second band part bent.

2. The endoscope electric connection device according to claim 1, wherein the first band part has a wider area than that of the second band part.

3. The endoscope electric connection device according to claim 1, wherein the first band part has a substantially rectangular form having long sides and short sides.

4. The endoscope electric connection device according to claim 3, wherein the second band part projects along the direction of the short sides from one side along the direction of the long sides of the first band part.

5. The endoscope electric connection device according to claim 4, wherein the second band part projects along the direction of the short sides from the substantial center of the side of the first band part.

6. The endoscope electric connection device according to claim 4, wherein the first band part bends in a second direction, which is different from a first direction that the second band part is bent.

7. The endoscope electric connection device according to claim 6, wherein the first direction is substantially orthogonal to the second direction and along the direction of the long sides.

8. The endoscope electric connection device according to claim 4, wherein the second band part has a guide portion for being fixed to the connector.

9. The endoscope electric connection device according to claim 3, wherein the first contact portion and second contact portion are aligned in the direction of the long sides of the first band part.

10. The endoscope electric connection device according to claim 1, wherein the first band part has the first contact portion and second contact portion on one surface and is kept bent to a substantially cylindrical form by the fixing portion with the surface inside.

11. The endoscope electric connection device according to claim 10, wherein the second contact portion is disposed on the side of the first band part where the second band part projects.

12. The endoscope electric connection device according to claim 11, wherein the first contact portion is disposed on the side of the first band part where the transmission cable connecting to the first band part extends.

13. The endoscope electric connection device according to claim 1, wherein the second band part has a guide portion for being fixed to the connector.

14. An endoscope electric connection device accommodated within a scope connector for connecting an electronic endoscope and an external apparatus, the device comprising:
- a first band part having a first contact portion to which a signal line of a transmission cable for transmitting an image signal from an image pickup unit of the electronic endoscope is connected and a second contact portion to which a ground line of the transmission cable is connected, and first band having flexibility;
- a fixing portion including a first cut groove formed as a cut end starting from one side on one end of the first band part and a second cut groove formed as a cut end starting from another side on another end of the first band part, wherein the bent state of the first band part is kept by the both ends of the first band part being engaged to each other such that the first and second cut grooves associate together;
- a second band part having a third contact portion connecting to a connector for electrically connecting to the external apparatus and having flexibility; and
- a transmitting portion provided in the first band part and second band part for electrically connecting the first contact portion and second contact portion to the third contact portion;
- wherein the transmitting portion can keep electric connection between the first contact portion and second contact portion and the third contact portion even with the first band part and the second band part bent.

15. An endoscope electric connection device accommodated within a scope connector for connecting an electronic and an external apparatus, the device comprising:
- a first band part having a first contact portion to which a signal line of a transmission cable for transmitting an image signal from an image pickup unit of the electronic endoscope is connected and a second contact portion to which a ground line of the transmission cable is connected, and first band having flexibility;
- a fixing portion including a first cut groove formed in an I-shape on one end of the first band part and a second cut groove formed in a c-shape on another end of the first band part, wherein the bent state of the first band part is kept by the both ends of the first band part being engaged to each other such that the first and second cut grooves associate together;
- a second band part having a third contact portion connecting to a connector for electrically connecting to the external apparatus and having flexibility; and
- a transmitting portion provided in the first band part and second band part for electrically connecting the first contact portion and second contact portion to the third contact portion;
- wherein the transmitting portion can keen electric connection between the first contact portion and second contact portion and the third contact portion even with the first band part and the second band part bent.

* * * * *